United States Patent
Shemesh

(10) Patent No.: US 8,709,269 B2
(45) Date of Patent: Apr. 29, 2014

(54) METHOD AND SYSTEM FOR IMAGING A CROSS SECTION OF A SPECIMEN

(75) Inventor: Dror Shemesh, Hod Hasharon (IL)

(73) Assignee: Applied Materials Israel, Ltd., Rehovot (IL)

( * ) Notice: Subject to any disclaimer, the term of this patent is extended or adjusted under 35 U.S.C. 154(b) by 771 days.

(21) Appl. No.: 12/103,458

(22) Filed: Apr. 15, 2008

(65) Prior Publication Data
US 2009/0053395 A1     Feb. 26, 2009

Related U.S. Application Data

(60) Provisional application No. 60/957,420, filed on Aug. 22, 2007.

(51) Int. Cl.
*H01J 37/08*     (2006.01)

(52) U.S. Cl.
USPC .................. 216/66; 250/492.1; 250/492.21; 216/62

(58) Field of Classification Search
USPC .................. 216/72, 66, 65, 59; 438/738, 735
See application file for complete search history.

(56) References Cited

U.S. PATENT DOCUMENTS

| | | | | |
|---|---|---|---|---|
| 4,693,779 A | * | 9/1987 | Okuhira et al. | 156/345.5 |
| 5,055,696 A | * | 10/1991 | Haraichi et al. | 250/492.2 |
| 6,162,735 A | * | 12/2000 | Zimmermann et al. | 438/712 |
| 6,207,553 B1 | * | 3/2001 | Buynoski et al. | 438/622 |
| 6,268,608 B1 | * | 7/2001 | Chandler | 250/492.2 |
| 6,670,610 B2 | | 12/2003 | Shemesh et al. | |
| 2003/0098416 A1 | * | 5/2003 | Shemesh et al. | 250/309 |
| 2005/0103746 A1 | | 5/2005 | Nadeau et al. | |
| 2006/0094132 A1 | * | 5/2006 | Liu et al. | 438/14 |
| 2006/0270239 A1 | * | 11/2006 | Triyoso et al. | 438/706 |
| 2007/0093044 A1 | | 4/2007 | Rijpers et al. | |

* cited by examiner

*Primary Examiner* — Duy Deo
*Assistant Examiner* — Erin Bergner
(74) *Attorney, Agent, or Firm* — Kilpatrick Townsend & Stockton LLP

(57) ABSTRACT

A method and a system for obtaining an image of a cross section of a specimen, the method includes: milling the specimen so as to expose a cross section of the specimen, in which the cross section comprises at least one first portion made of a first material and at least one second portion made of a second material; smoothing the cross section; performing gas assisted etching of the cross section so as generate a topography difference between the at least one first portion and the at least one second portion of the cross section; coating the cross section with a thin layer of conductive material; and obtaining an image of the cross section; wherein the milling, smoothing, performing, coating and obtaining are performed while the specimen is placed in a vacuum chamber.

21 Claims, 11 Drawing Sheets

METHOD AND SYSTEM FOR IMAGING A CROSS SECTION OF A SPECIMEN

RELATED APPLICATIONS

This application is a nonprovisional of, incorporates by reference and claims the priority benefit of U.S. Provisional Patent Application No. 60/957,420, filed Aug. 22, 2007.

FIELD OF THE INVENTION

The invention relates to methods and systems for imaging a cross section of a specimen.

BACKGROUND OF THE INVENTION

In the study of electronic materials and processes for fabricating such materials into an electronic structure, a specimen of the electronic structure is frequently used for microscopic examination for purposes of failure analysis and device validation. For instance, a specimen of an electronic structure such as a silicon wafer is frequently analyzed in a scanning electron microscope (SEM) and transmission electron microscope (TEM) to study a specific characteristic feature in the wafer. Such a characteristic feature may include the circuit fabricated and any defects formed during the fabrication process. An electron microscope is one of the most useful pieces of equipment for analyzing the microscopic structure of semiconductor devices.

In preparing specimens of an electronic structure for electron microscopic examination, various polishing and milling processes can be used to section the structure until a specific characteristic feature is exposed.

As device dimensions are continuously reduced to the sub-half-micron level, the techniques for preparing specimens for study in an electron microscope have become more important. The conventional methods for studying structures by an optical microscope cannot be used to study features in a modern electronic structure due to the unacceptable resolution of an optical microscope.

Although TEM techniques can provide a higher resolution image and a more detailed description of the internal structure of a specimen than is available using SEM techniques, they are only effective for electron transparent samples. Thus it is a basic requirement for TEM samples that the sample must be thin enough to be penetrated by the electron beam and thin enough to avoid multiple scattering, which causes image blurring. Nonetheless, it is recognized in the art that thin samples extracted from wafers may be brittle, and subject to fracture or crumbling. Furthermore, the fragile nature of thin extracted samples means that processes for extracting thin samples are difficult to automate, thus hindering efforts to automate these processes. In addition, TEM sample preparation and TEM imaging processes are usually time consuming and cannot be done in-line. In this process, the TEM sample has to be prepared, lifted-out from the wafer and put on a TEM sample holder, before it is ready for TEM imaging.

A dual column system, incorporating a scanning electron microscope and a focused ion beam (FIB) unit, can produce high resolution SEM images of a localized cross section. Typical FIB units are those manufactured by Applied Materials (Applied Materials, Santa Clara, Calif.) including the SEMVision™ G2 FIB and those available from FEI Company of Hillsboro, Oreg., including models 200, 820, 830, or 835. The skilled practitioner is referred also to U.S. Pat. No. 6,670,610 of Shemesh et al, titled "System and Method for Directing a Miller." A typical dual column system includes a SEM column, a FIB column, a supporting element that supports the wafer and a vacuum chamber in which the wafer is placed while being milled (by the FIB column) and while being imaged (by the SEM column).

The cross section of a wafer is produced by: (i) locating a location of interest that should be milled in order to expose a cross section of the wafer, in which the locating is usually found by navigation of the SEM and sometimes also an optical microscope, (ii) moving the wafer (by a mechanical supporting element) so that the wafer is located under the FIB unit, and (iii) milling the wafer to expose the cross section. The cross-section is exposed by forming a small hole in the wafer (usually sized a few microns to few tens of microns in lateral and vertical dimensions). The cross section is usually vertical, so that the SEM should be tilted in order to image the cross section.

Today the resolution of a cross-section image generated by an SEM is limited to a few nanometers. The resolution is limited due to the charging effects of non-conductive (or partially conductive) materials of the wafer. The resolution is also limited due to the relatively large volume that emits electrons in response to an interaction with a charged particle beam. This volume is also referred to as an information volume.

It is noted that advanced FAB processes involve thin layers beyond the SEM resolution limit. In addition, the cross-section may include portions made of materials that cannot be distinguished by SEM imaging. For example, different types of dielectric layers appear on the SEM image with similar gray level, so that they are practically irresolvable.

The resolution of cross section images can be improved and the distinction between materials (also referred to as contrast) can be improved by various prior art processes.

One prior art process that improves the resolution and the material distinctiveness is complex and time consuming. It includes the following stages: (i) cross sectioning the wafer by breaking the wafer into samples, (ii) polishing the wafer sample of interest up to the required surface, (iii) performing wet etching by immersing the wafer sample in a solution (for example HF), (iv) coating the cross section with conductive material (such as Gold or Chrome of about 1 nanometer) and (v) imaging the (now coated) cross section.

This prior art process provides a cross section that has a fine topography that distinguishes between different materials (during the wet etch process different materials are etched at a different rate), and is coated with a conductive material so as to reduce charging effects and reduces the information volume (which is substantially limited to the conductive layer).

This mentioned above process has a few drawbacks, such as but not limited to the following: (i) wet etch cannot be executed within the vacuum chamber of a SEM (or of a dual column tool); (ii) the breaking of the wafer is destructive; and (iii) the overall process is complex and time consuming as the wafer has to be broken, polished, placed in a wet etch chamber, etched, removed from the wet etch chamber, placed into a material deposition chamber, coated with material, removed from the material deposition chamber, placed into the vacuum chamber of the SEM, and imaged.

Other techniques for milling a wafer are illustrated in US patent application publication serial number 2005/0103746 of Nadeau et al. and in US patent application publication serial number 2007/0093044 of Rijpers et al.

There is a growing need to provide fast and efficient methods and systems for imaging a cross section of a specimen.

SUMMARY OF THE INVENTION

A method for obtaining an image of a cross section of a specimen, the method includes: (i) milling the specimen so as to expose a cross section of the specimen, in which the cross section comprises at least one first portion made of a first material and at least one second portion made of a second material; (ii) smoothing the cross section; (iii) performing gas assisted etching of the cross section so as to generate a topography difference between the at least one first portion and the at least one second portion of the cross section; (iv) coating the cross section with a thin layer of conductive material; and (v) obtaining an image of the cross section, wherein the milling, smoothing, performing, coating and obtaining are performed while the specimen is placed in a vacuum chamber Conveniently, the method includes performing gas assisted etching by exposing a light activated etchant gas to light.

Conveniently, the method includes focusing light onto an area that is either proximate to the cross section or comprises at least a portion of the cross section.

Conveniently, the area is located within a field of view of a charged particle beam column utilized for obtaining the image of the cross section.

Conveniently, the area is located outside a field of view of a charged particle beam column utilized for obtaining the image of the cross section.

Conveniently, the gas assisted etching includes exposing the light activated etchant gas to light that has a wavelength that does not exceed 200 nanometers. It is noted that the wavelength of the light can exceed 200 nanometers. It is further noted that non-monochromatic light that spans a range of wavelengths can be used. The range can include wavelengths above 200 nanometers, below 200 nanometers or a combination thereof.

Conveniently the method includes performing gas assisted etching by exposing a charged particle beam activated etchant gas to a charged particle beam.

Conveniently, the method includes performing gas assisted etching by exposing gas to a pulsed light.

Conveniently, the milling includes milling the specimen by a focused ion beam generated by a focused ion beam column that is coupled to the vacuum chamber, wherein the obtaining of the image comprises illuminating the cross section by an electron beam generated by a scanning electron microscope column that is coupled to the vacuum chamber and the scanning electron microscope column is substantially parallel to the focused ion beam column.

Conveniently, the coating comprises performing gas assisted coating.

Conveniently, the stage of performing the gas assisted etching comprises spraying an etchant gas onto an area that is either proximate to the cross section or comprises the cross section.

A cross section imaging system includes at least one charged particle beam column coupled to a vacuum chamber. The system is adapted to: (i) mill the specimen so as to expose a cross section of the specimen, whereas in which the cross section comprises at least one first portion made of a first material and at least one second portion made of a second material; (ii) smooth the cross section; (iii) perform gas assisted etching of the cross section so as generate a topography difference between the at least one first portion and the at least one second portion of the cross section; (iv) coat the cross section with a thin layer of conductive material; and (v) obtain an image of the cross section, wherein the specimen is located within the vacuum chamber while the specimen is milled, while the cross section is smoothed, while gas assisted etching is performed, while the cross section is coated and while the image is obtained. The specimen is milled, the cross section is smoothed, the cross section is coated and the image of the cross section is obtained by utilizing at least one charged particle beam generated by the at least one charged particle beam column.

Conveniently, the system includes an illumination unit, wherein the system mills the specimen by directing light generated by the illumination unit towards light activated etchant gas.

Conveniently, the illumination unit comprises focusing optics that focus the light onto an area that is either proximate to the cross section or comprises at least a portion of the cross section.

Conveniently, the area is located within a field of view of a charged particle beam column.

Conveniently, the area is located outside each field of view of each of the at least one charged particle beam column.

Conveniently, the illumination unit generates light that has a wavelength that does not exceed 200 nanometers.

Conveniently, the system is adapted to expose a charged particle beam activated etchant gas to a charged particle beam generated by a charged particle beam column.

Conveniently, the illumination unit generates pulsed light.

Conveniently, the at least one charged particle beam column comprises a focused ion beam column and a scanning electron microscope column, wherein the scanning electron microscope column is substantially parallel to the focused ion beam column, the scanning electron microscope column images the cross section, and the focused ion beam column mills the specimen and smoothes the cross section.

Conveniently, the system includes a gas conduit adapted to provide gas during a gas assisted coating of the cross section.

Conveniently, the system includes a spraying unit adapted to spray an etchant gas onto an area that is either proximate to the cross section or comprises the cross section.

BRIEF DESCRIPTION OF THE DRAWINGS

In order to understand the invention and to see how it may be carried out in practice, an embodiment will now be described, by way of non-limiting example only, with reference to the accompanying drawings, in which.

DETAILED DESCRIPTION OF THE DRAWINGS

It should be understood that the class of embodiments described herein provides only a few examples of the many advantageous uses of the innovative teachings herein. In general, statements made in the specification of the present application do not necessarily delimit any of the various claimed inventions. Moreover, some statements may apply to some inventive features but not to others. In accordance with many embodiments of the present invention, a disclosed method for sample formation begins with the cutting of a portion of a specimen. In one specific embodiment, the specimen is a semiconductor wafer, although in other embodiments, exemplary specimens include a biological material, a micromechanical device, a thin film, etc.

The mentioned below systems and methods achieve a resolution and material contrast comparable to that achieved by wafer breakage (the second method described above), without breaking the wafer. A cross section is formed, smoothed, selectively etched, coated and imaged without removing the wafer from a vacuum chamber.

According to one embodiment of the invention the system includes multiple columns. For example, the system can include a FIB column and a SEM column. According to another embodiment of the invention the system includes only one column. For example, if the system includes only a SEM column it is expected that the milling process will be slower (in comparison to FIB milling). For simplicity of explanation the following example will refer to a dual column system in which a SEM column images the cross section and the FIB column mills the wafer and smoothes the cross section. Those of skill in the art will appreciate that the SEM column can remove material (and/or smooth the cross section) and that the FIB column can image the cross section.

It is noted that each of the mentioned below systems can perform a calibration process and each of the mentioned below methods can include a calibration stage. During the calibration stage various parameters of the system such as FIB column parameters, light source parameters, SEM column parameters and gas parameters (or a combination thereof) can be varied. These parameters can include light wavelength, light coherence, light intensity, light modulation, light polarization, charged particle beam current, charged particle beam column voltages, spot size, scan or spot mode of charged particle beam, gas type and gas pressure. The calibration process can optimize the coating stage, the milling stage, the imaging stage, the etching stage and the like. For example, one or more of these mentioned above parameters can be selected in order to provide a homogeneous deposition process that has the correct thickness.

It is noted that all figures are out of scale and that the terms "first" and "second" are used to differentiate between one portion from another or one material from another.

Charged Particle Beam Activated Gas Assisted Etching

Figure 1A:
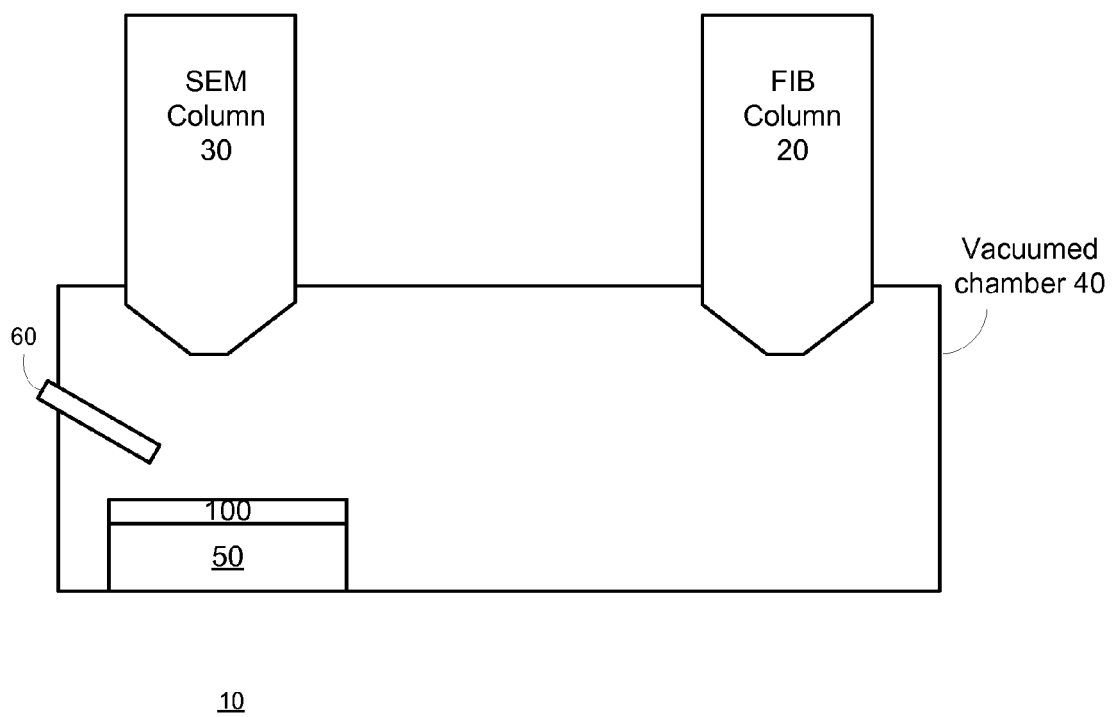
FIG. 1a illustrates a system for imaging a cross section according to an embodiment of the invention.

FIG. 1a illustrates system 10 for imaging a cross section according to an embodiment of the invention.

System 10 includes FIB column 20, SEM column 30, vacuum chamber 40, supporting element 50 and gas supply unit 60. FIB column 20 and SEM column 30 are connected to vacuum chamber 40 so that a charged particle beam generated by either one of these charged particle columns propagates (before impinging on wafer 100) through a vacuumed environment formed within vacuum chamber 40.

System 10 performs gas assisted etching by exposing a charged particle beam activated etchant gas to an electron beam generated by SEM column 30.

A specimen (such as wafer 100) is supported by supporting element 50 and also transferred (within vacuum chamber 40) by supporting element 50. FIB column 20 can mill wafer 100 to form a cross section and also smoothes the cross section. The smoothing conveniently involves utilizing smaller acceleration voltages in relation to the milling of wafer 100. The cross section includes one or more first portions made of a first material and one or more second portions made of a second material. It is noted that the cross section can also be made of additional portions made of other materials.

System 10 then performs gas assisted etching of the cross section so as to generate a topography difference between the at least one first portion and the at least one second portion of the cross section. During this stage gas supply unit 60 supplies charged particle beam activated gas to an area that can include the cross section or can be proximate to the cross section.

According to an embodiment of the invention the charged particle beam activated gas is an electron beam activated gas. SEM column 30 exposes the electron beam activated gas to an electron beam so as to activate the electron beam activated gas.

According to an embodiment of the invention the charged particle beam activated gas is an ion activated gas. FIB column 20 exposes the ion beam activated gas to an ion beam so as to activate the ion beam activated gas.

The charged particle activated gas is non-reactive or slightly reactive in the absence of a charged particle beam. It becomes reactive after exposure to the charged particle beam and etches different materials at different rates, so that a fine topography is created.

Usually an electron beam that has an energy level of a few thousand of electron volts (few keV) is used in order to activate an electron beam activated gas. In the case of using an ion beam activated gas, it is convenient to use an ion beam of low energy (for example—about a few hundred electron volts).

Figure 1B:
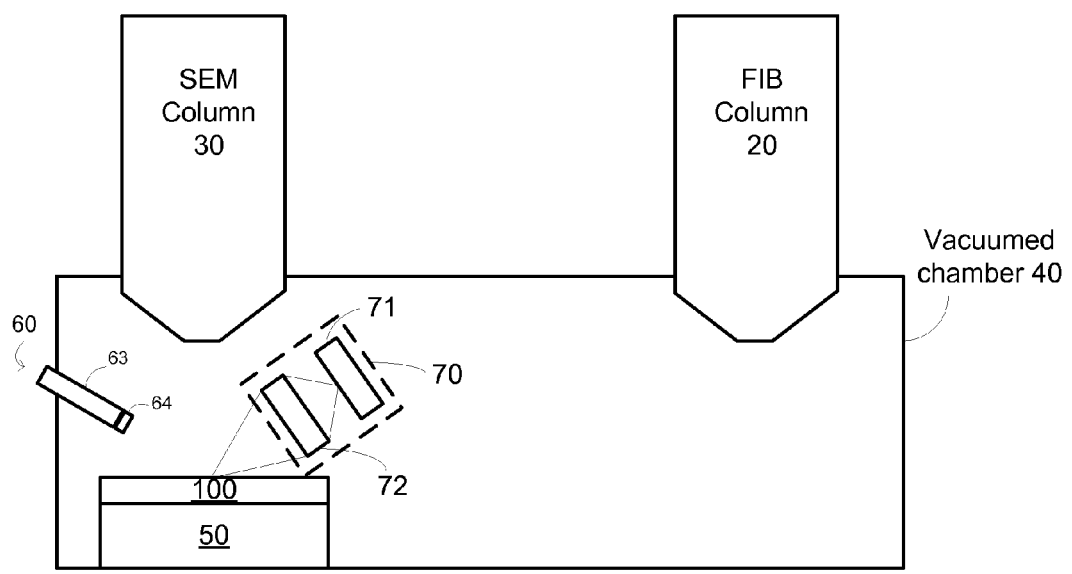
FIG. 1b illustrates a system for imaging a cross section according to another embodiment of the invention.
Figure 1C:
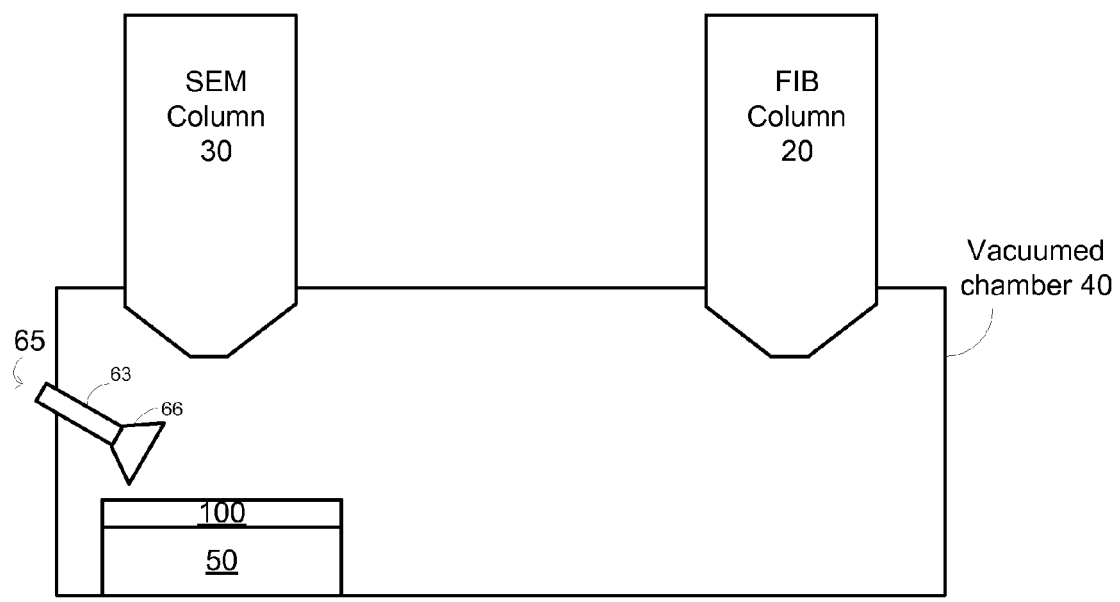
FIG. 1c illustrates a system for imaging a cross section according to a further embodiment of the invention.
Figure 1D:
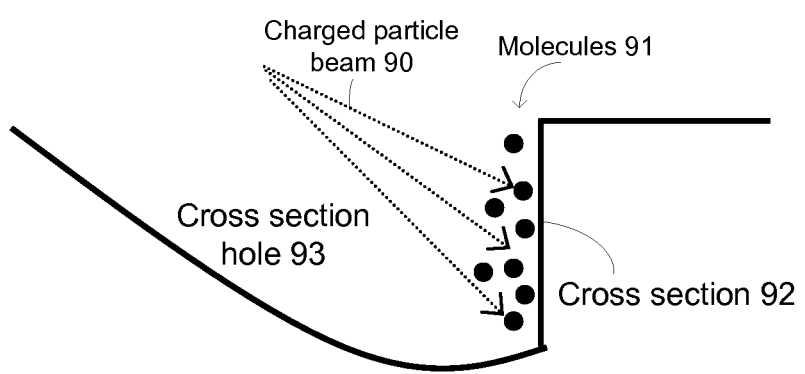
FIG. 1d illustrates a gas assisted etching according to an embodiment of the invention.

FIG. 1d illustrates molecules 91 of a charged particle beam activated etchant gas that etch cross section 92 as a result of an interaction with one or more charged particle electron beams 90. Cross section 92 is exposed after milling the specimen to form cross section hole 93.

Figure 2A:
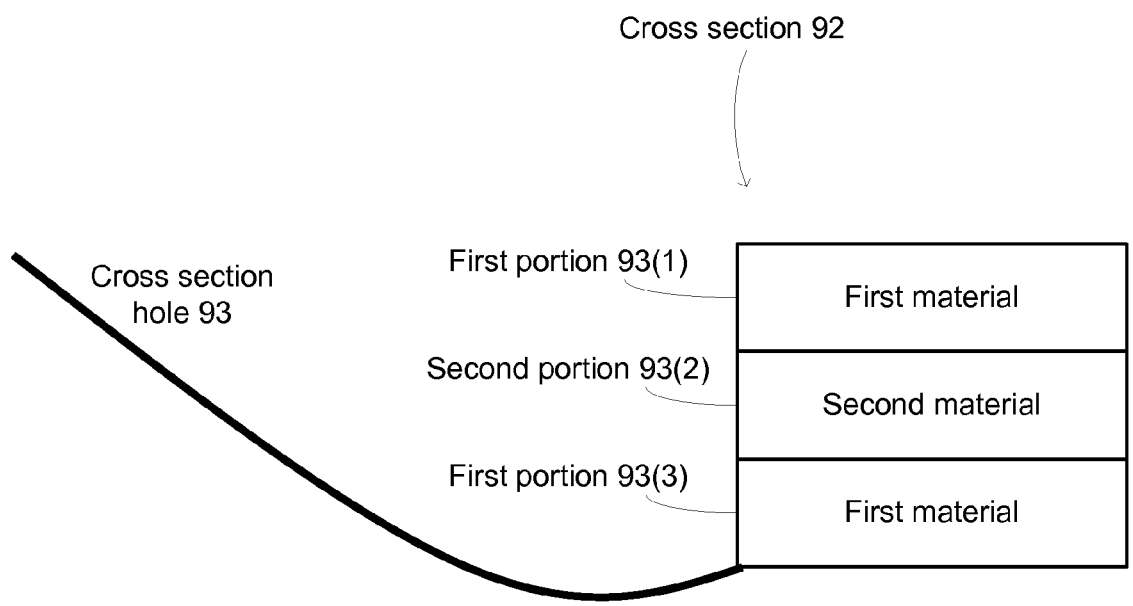
FIG. 2a illustrates a cross section of a sample before applying the gas assisted etching and FIG. 2b illustrates the cross section after applying the gas assisted etching according to an embodiment of the invention.
Figure 2B:
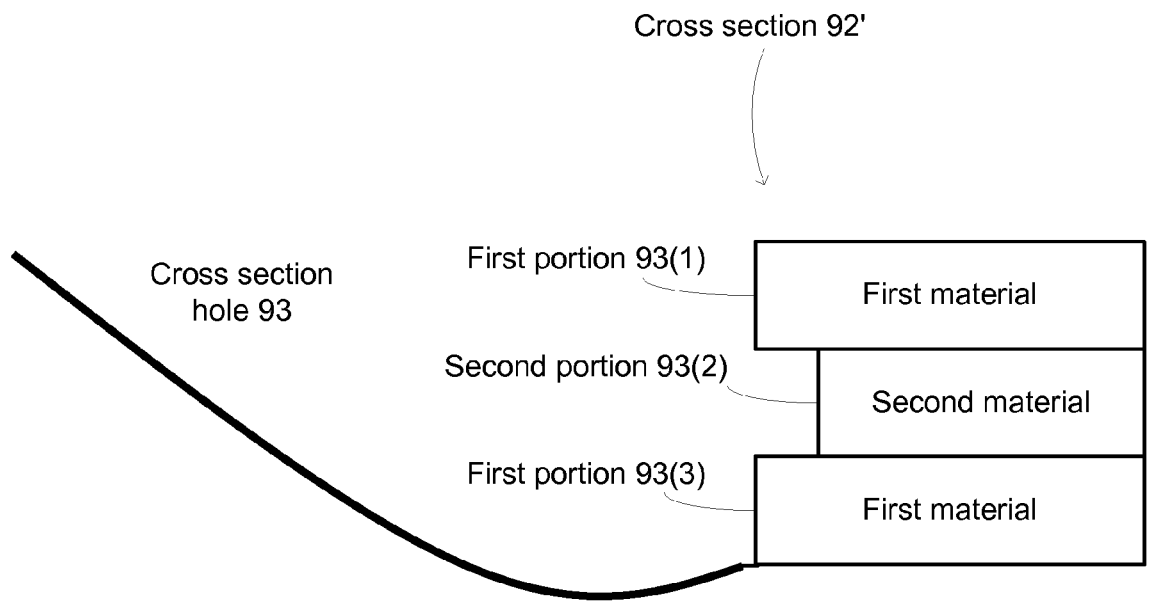

FIG. 2a illustrates cross section 92 before and after the etching. Before the etching, cross section 92 is smooth. After etching the cross section, a fine topography was is formed as second portion 93(2) (that is made of a second material) is etched at a higher rate than first portions 93(1) and 93(3) (that are made of a first material).

After the selective etch process, system 10 coats the cross section with a thin layer of conductive material, system 10 can apply a gas assisted coating process (by using gas supply unit 60) in which gas interacts with a charged particle beam in order to depose material on the cross section.

Conveniently, system 10 can inject gases that can deposit conductive materials such as Tungsten and Platinum. The gas can be non-reactive in the absence of an electron beam or an ion beam, and becomes reactive when interacting with such a charged particle beam. It is noted that other gases can be used to deposit other type types of conductive material on the cross-section surface.

After the cross section is coated, SEM column 30 scans the cross section in order to obtain an image of the cross section. The image is obtained by processing detection signals from one or more detectors (not shown) of system 10. Scanning an area and obtaining SEM images is known in the art and requires no further explanation. It is noted that after the cross section is coated, FIB column 20 can scan the cross section in order to obtain an image of the cross section.

It is noted that supporting element 50 can move wafer 100 from a location in which wafer 100 (and especially the cross section) are within the field of view of SEM column 30 to a location in which wafer 100 (and especially the cross section) are within the field of view of FEB column 20.

Gas supply unit 60 can be used for supplying charged particle beam activated gas and a gas that is used during a gas assisted coating process. It is noted that the same pipe can be used to provide these gases but this is not necessarily so. It is noted that gas supply unit 60 can include gas reservoirs, gas sources, valves, one or more inlets and one or more outlets. For simplicity of explanation, gas supply unit 60 is illustrated as a pipe.

Figure 6A:
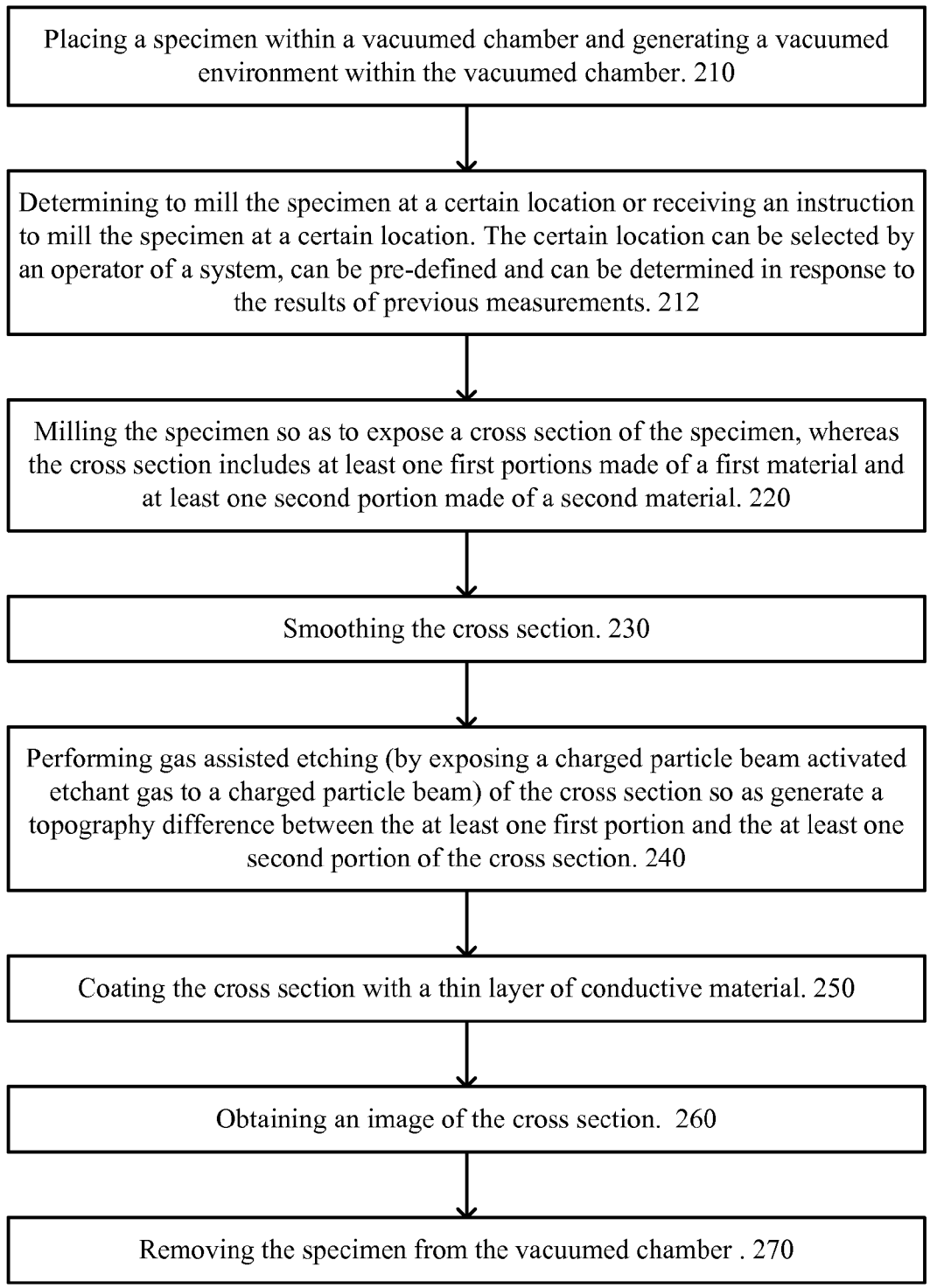
FIG. 6a illustrates a method for imaging a cross section of a specimen according to an embodiment of the invention.

FIG. 6a illustrates method 200 for imaging a cross section of a specimen according to an embodiment of the invention.

Method 200 starts by stage 210 of placing a specimen within a vacuum chamber and generating a vacuum environment within the vacuum chamber. Stages 220, 230, 240, 250 and 260 are executed while the specimen is located within the vacuum chamber. Conveniently, one or more cross sections are formed and imaged without removing the specimen from the vacuum chamber.

Method 200 also includes stage 212 of determining to mill the specimen at a certain location or to receive an instruction to mill the specimen at a certain location. The certain location can be selected by an operator of a system, can be pre-defined and can be determined in response to the results of previous measurements. Stage 212 can precede stage 210, can follow stage 210 and can be executed in parallel to stage 210. For simplicity of explanation, stage 212 is illustrated as following stage 210.

Stage 212 is followed by stage 220 of milling the specimen so as to expose a cross section of the specimen, in which the cross section includes at least one first portion made of a first material and at least one second portion made of a second material. Stage 220 can include locating the location to be milled and then milling that location to expose the cross section by utilizing a charge particle beam.

Stage 220 is followed by stage 230 of smoothing (fine milling) the cross section.

Stage 230 is followed by stage 240 of performing gas assisted etching (by exposing a charged particle beam activated etchant gas to a charged particle beam) of the cross section so as generate a topography difference between the at least one first portion and the at least one second portion of the cross section.

Stage 240 is followed by stage 250 of coating the cross section with a thin layer of conductive material. Stage 250 can involve gas assisted coating.

Stage 250 is followed by stage 260 of obtaining an image of the cross section.

It is noted that stage 260 can be followed by removing the specimen from the vacuum chamber (stage 270) or can be followed by stage 220 so that another cross section is formed and imaged.

It is further noted that method 200 can be executed by system 10 but this is not necessarily so. For example, a single charged particle beam column system can implement method 200.

Conveniently, stage 220 of milling includes milling the specimen by a focused ion beam generated by a focused ion beam column that is coupled to the vacuum chamber. Conveniently, stage 260 includes illuminating the cross section by an electron beam generated by a scanning electron microscope column that is coupled to the vacuum chamber. The scanning electron microscope column can be substantially parallel to the focused ion beam column.

Light Activated Gas Assisted Etching

FIG. 1b illustrates system 11 for imaging a cross section according to an embodiment of the invention.

System 11 includes FIB column 20, SEM column 30, vacuum chamber 40, supporting element 50, gas supply unit 60 and illumination unit 70. FIB column 20 and SEM column 30 are connected to vacuum chamber 40 so that a charged particle beam generated by either one of these charged particle columns propagates (before impinging on wafer 100) through a vacuum environment formed within vacuum chamber 40.

System 11 performs gas assisted etching by exposing a light activated etchant gas to light generated by illumination unit 70. Illumination unit 70 can include a light source such as light source 71 and can also include focusing optics such as focusing optics 72. Each of these components (71, 72) can be located within vacuum chamber 40 but this is not necessarily so. Light source 71 can be a monochromatic light source, a broadband light source, a pulsed light source, a continuous light source, can be a laser, a lamp (such as but not limited to a Mercury lamp) and can generate a light at wavelengths that do not exceed 200 nanometers, but this is not necessarily so.

Focusing optics 72 focuses the light onto an area that can include a cross section, can include only a portion of the cross section and can be located in proximity to the cross section. For example, the area can be located a few nanometers or as few microns from the cross section. It is noted that even when a light beam is focused onto the cross section, the beam may pass through light activated etchant gas that is not located near the cross section.

By focusing the light beam onto the mentioned above area, selective etching occurs (mainly or only) near the cross section while other portions of the wafer are not substantially (or even non-substantially) etched.

Conveniently, light activated gas is guided through gas supply unit 60 and especially through pipe 63 of gas supply unit 60. Pipe 63 is connected to nozzle 64 that is located close to wafer 100. Usually, gas pipe 63 is heated, to avoid material condensation inside pipe 63. Conveniently, light activated gases can include but are not limited to $XeF_2$, $NF_3$ or $SF_6$.

The wavelength of the light depends on the activation energy of the light activated gas. Conveniently, wavelength in the range of 200 nm or less should be used in order to create an efficient activation process. It is noted that different pipes can be used for providing the light activated etchant gas and the gas used during a gas assisted coating process but this is not necessarily so.

It is noted that gas supply unit 60 can include gas reservoirs, gas sources, valves, one or more inlets and one or more outlets. For simplicity of explanation gas supply unit 60 is illustrated as including pipe 63 and nozzle 64.

A specimen (such as wafer 100) is supported by supporting element 50 and also transferred (within vacuum chamber 40) by supporting element 50. FIB column 20 can mill wafer 100 to form a cross section and also smoothes the cross section. The smoothing conveniently involves utilizing smaller acceleration voltages in relation to the milling of wafer 100. The cross section includes one or more first portions made of a first material and one or more second portions made of a second material. It is noted that the cross section can also be made of additional portions made of other materials.

System 11 then performs gas assisted etching of the cross section so as to generate a topography difference between the at least one first portion and the at least one second portion of the cross section. During this stage, gas supply unit 60 supplies light activated gas to an area that can include the cross section or can be proximate to the cross section.

The light activated gas is a non-reactive or slightly reactive in the absence of light. It becomes reactive after exposure to the light and etches different materials at different rates, so that a fine topography is created.

After the selective etch process system 11 coats the cross section with a thin layer of conductive material, system 11 can apply a gas assisted coating process in which gas interacts with a charged particle beam in order to depose material on the cross section.

Conveniently, system 11 can inject gases that can deposit conductive materials such as Tungsten and Platinum. The gas can be non-reactive in the absence of an electron beam or an ion beam, and becomes reactive when interacting with such a charged particle beam. It is noted that other gases can be used to deposit other type types of conductive material on the cross-section surface.

After the cross section is coated, SEM column 30 scans the cross section in order to obtain an image of the cross section. The image is obtained by processing detection signals from one or more detectors (not shown) of system 11. Scanning an area and obtaining SEM images is known in the art and requires no further explanation. It is noted that after the cross section is coated FIB column 20 can scan the cross section in order to obtain an image of the cross section.

It is noted that supporting element 50 can move wafer 100 from a location in which wafer 100 (and especially the cross section) are within the field of view of SEM column 30 to a location in which wafer 100 (and especially the cross section) are within the field of view of FIB column 20.

Figure 3:
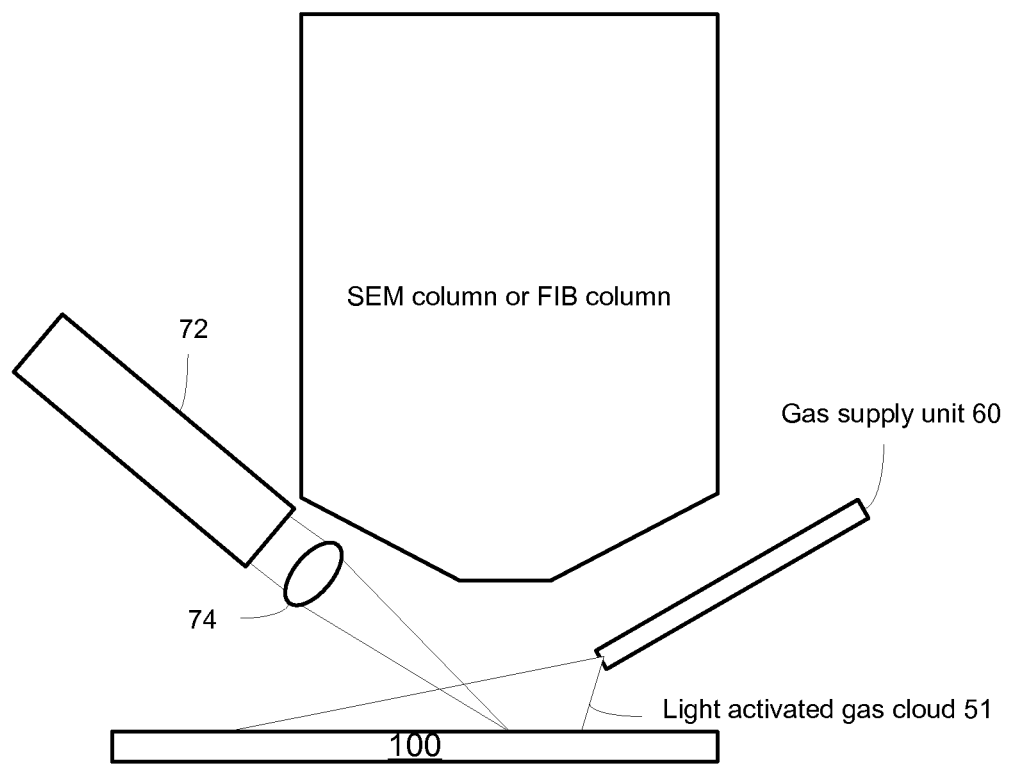
FIG. 3 illustrates an illumination unit that exposes a light activated etchant gas to light during a gas assisted etching process according to an embodiment of the invention.
Figure 4:
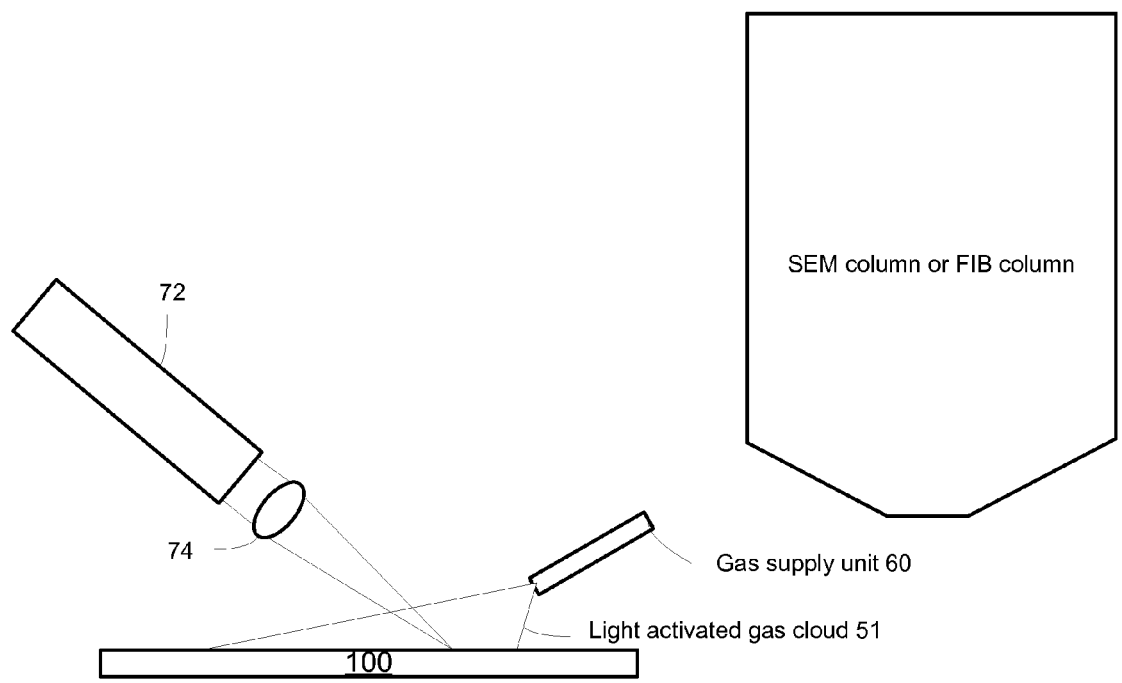
FIG. 4 illustrates an illumination unit that exposes a light activated etchant gas to light during a gas assisted etching process according to another embodiment of the invention.

It is further noted that during the gas assisted etching process the cross section can be located within a field of view of one of the charged particle beam columns (as illustrated in FIG. 3) or outside the field of view of these charged particle beam columns (as illustrated in FIG. 4). FIG. 3 and 4 illustrate a light activated gas cloud 51.

Figure 6B:
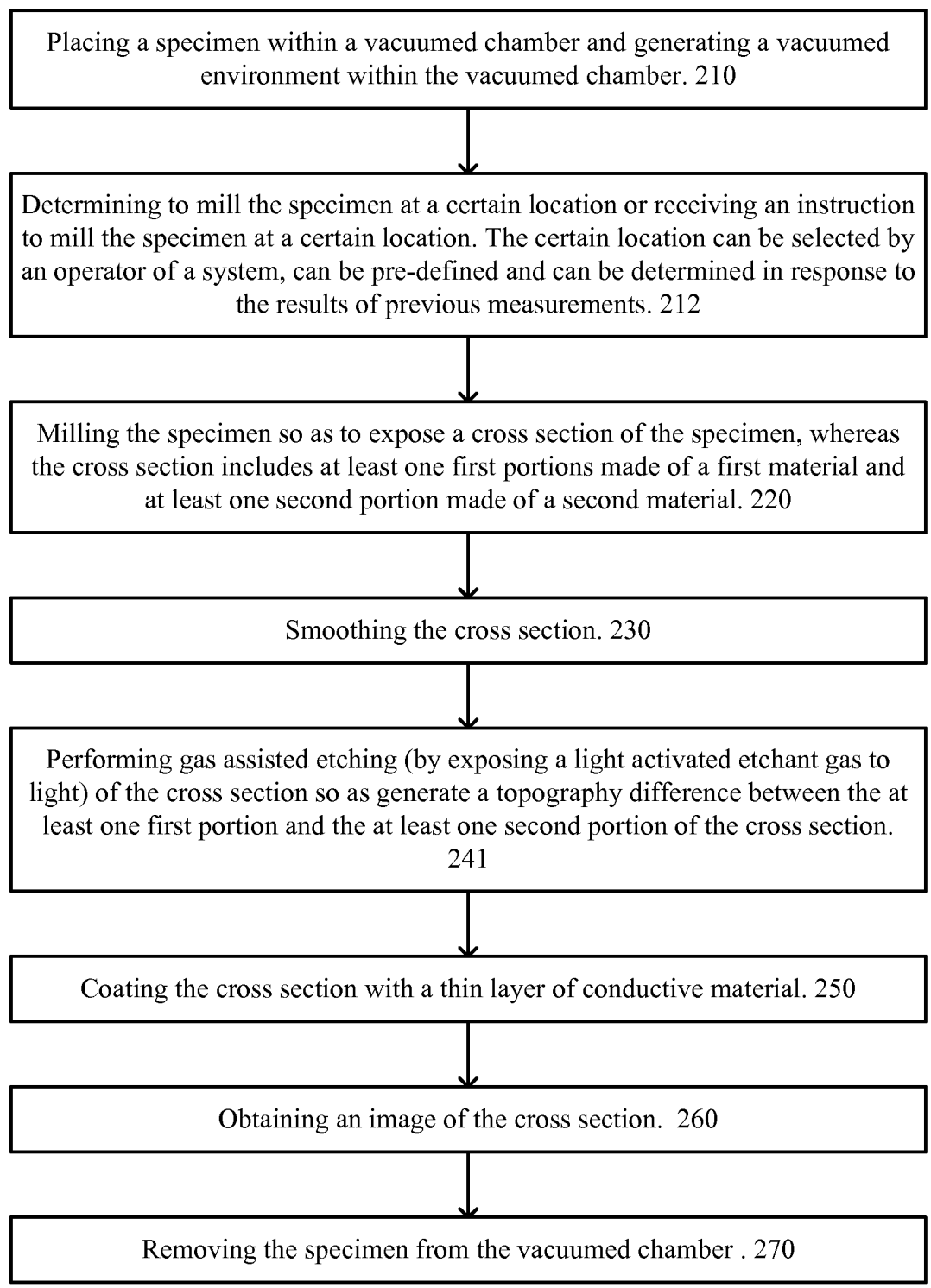
FIG. 6b illustrates a method for imaging a cross section of a specimen according to another embodiment of the invention.

FIG. 6b illustrates method 201 for imaging a cross section of a specimen according to an embodiment of the invention.

Method 201 starts by stage 210 of placing a specimen within a vacuum chamber and generating a vacuum environment within the vacuum chamber. Stages 220, 230, 241, 250 and 260 are executed while the specimen is located within the vacuum chamber. Conveniently, one or more cross sections are formed and imaged without removing the specimen from the vacuum chamber.

Method 201 also includes stage 212 of determining to mill the specimen at a certain location or to receive an instruction to mill the specimen at a certain location. The certain location can be selected by an operator of a system, can be pre-defined and can be determined in response to the results of previous measurements. Stage 212 can precede stage 210, can follow stage 210 and can be executed in parallel to stage 210. For simplicity of explanation stage 212 is illustrated as following stage 210.

Stage 212 is followed by stage 220 of milling the specimen so as to expose a cross section of the specimen, in which the cross section includes at least one first portion made of a first material and at least one second portion made of a second material. Stage 220 can include locating the location to be milled and then milling that location to expose the cross section by utilizing a charge particle beam.

Stage 220 is followed by stage 230 of smoothing the cross section.

Stage 230 is followed by stage 241 of performing gas assisted etching (by exposing a light activated etchant gas to light) of the cross section so as to generate a topography difference between the at least one first portion and the at least one second portion of the cross section.

Conveniently, stage 241 includes focusing light onto an area that is either proximate to the cross section or comprises at least a portion of the cross section. According to an embodiment of the invention, the area is located within a field of view of a charged particle beam column utilized for obtaining the image of the cross section. According to another embodiment of the invention, the area is located outside a field of view of a charged particle beam column utilized for obtaining the image of the cross section.

Stage 241 can include exposing the light activated gas to monochromatic light, to broadband light, to light pulses, to a continuous flux of light, to light generated by a laser, to light generated by a lamp (such as but not limited to a Mercury lamp) and especially to light at wavelengths that do not exceed 200 nanometers.

Stage 241 is followed by stage 250 of coating the cross section with a thin layer of conductive material. Stage 250 can involve gas assisted coating.

Stage 250 is followed by stage 260 of obtaining an image of the cross section.

It is noted that stage 260 can be followed by removing the specimen from the vacuum chamber (stage 270) or can be followed by stage 220 so that another cross section is formed and imaged.

It is further noted that method 201 can be executed by system 11 but this is not necessarily so. For example, a single charged particle beam column system can implement method 201.

Conveniently, stage 220 of milling includes milling the specimen by a focused ion beam generated by a focused ion beam column that is coupled to the vacuum chamber. Conveniently, stage 260 includes illuminating the cross section by an electron beam generated by a scanning electron microscope column that is coupled to the vacuum chamber. The scanning electron microscope column can be substantially parallel to the focused ion beam column.

Spray Based Etching

FIG. 1c illustrates system 12 for imaging a cross section according to an embodiment of the invention.

System 12 includes FIB column 20, SEM column 30, vacuum chamber 40, supporting element 50, and gas supply unit 65 that includes pipe 63 and spraying unit 66. FIB column 20 and SEM column 30 are connected to vacuum chamber 40 so that a charged particle beam generated by either one of these charged particle columns propagates (before impinging on wafer 100) through a vacuum environment formed within vacuum chamber 40.

It is noted that gas supply unit 65 can include gas reservoirs, gas sources, valves, one or more inlets and one or more outlets. For simplicity of explanation gas supply unit 65 is illustrated as including pipe 63 and spraying unit 66.

Spraying unit 66 includes a nozzle that sprays an etchant gas on the cross section in order to etch the cross section and to provide the mentioned above fine topography. The etching gas acts spontaneously, without being activated by an electron beam, an ion beam, or light. Therefore, the nozzle does not need to be located in a position that is responsive to the path of a charged particle beam (as in the case of using a charged particle beam activated gas) or of a light beam (in case of using light activated gas).

A specimen (such as wafer 100) is supported by supporting element 50 and also transferred (within vacuum chamber 40)

by supporting element 50. FIB column 20 can mill wafer 100 to form a cross section and also smoothes the cross section. The smoothing conveniently involves utilizing smaller acceleration voltages in relation to the milling of wafer 100. The cross section includes one or more first portions made of a first material and one or more second portions made of a second material. It is noted that the cross section can also be made of additional portions made of other materials.

System 12 then performs gas assisted etching of the cross section so as generate a topography difference between the at least one first portion and the at least one second portion of the cross section. During this stage, gas supply unit 65 and especially spraying unit 66 sprays etchant gas to an area that can include the cross section or can be proximate to the cross section.

The etchant gas is reactive and etches different materials at different rates, so that the fine topography is created.

After the selective etch process system 12 coats the cross section with a thin layer of conductive material, system 12 can apply a gas assisted coating process in which gas interacts with a charged particle beam in order to depose material on the cross section.

Conveniently, system 12 can inject gases that can deposit conductive materials such as Tungsten and Platinum. The gas can be non-reactive in the absence of an electron beam or an ion beam, and becomes reactive when interacting with such a charged particle beam. It is noted that other gases can be used to deposit other types of conductive material on the cross-section surface.

After the cross section is coated, SEM column 30 scans the cross section in order to obtain an image of the cross section. The image is obtained by processing detection signals from one or more detectors (not shown) of system 12. Scanning an area and obtaining SEM images is known in the art and requires no further explanation. It is noted that after the cross section is coated FIB column 20 can scan the cross section in order to obtain an image of the cross section.

It is noted that supporting element 50 can move wafer 100 from a location in which wafer 100 (and especially the cross section) are within the field of view of SEM column 30 to a location in which wafer 100 (and especially the cross section) are within the field of view of FIB column 20.

Figure 5:
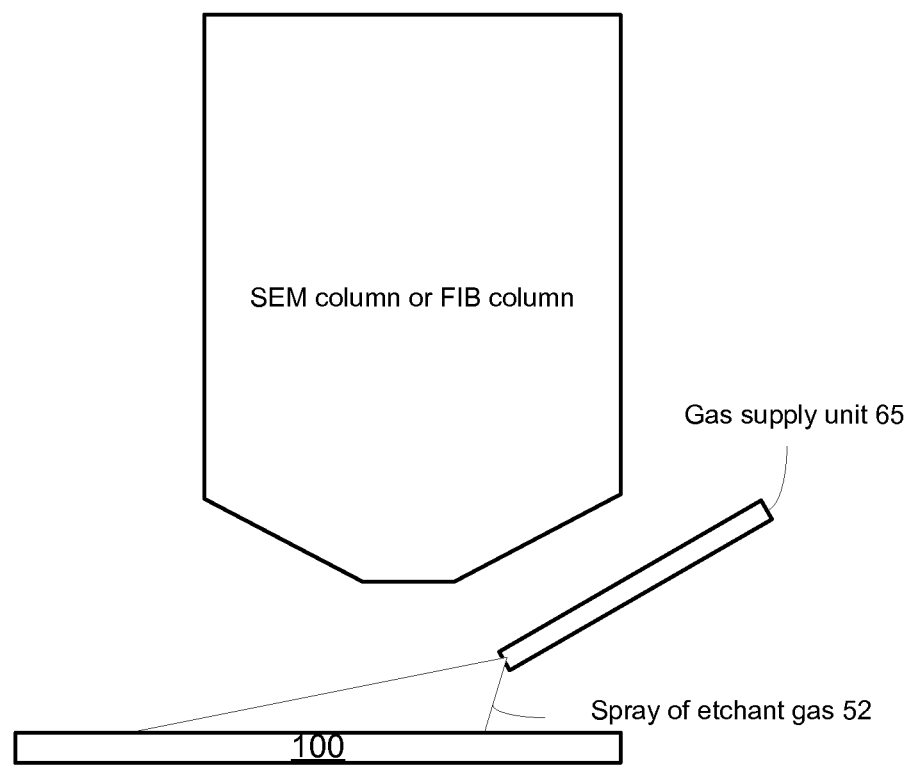
FIG. 5 illustrates a spraying unit that sprays etchant gas during a gas assisted etching process according to an embodiment of the invention.

It is further noted that during the gas assisted etching process the cross section can be located within a field of view of one of the charged particle beam columns (as illustrated in FIG. 5) or outside the field of view of these charged particle beam columns.

Figure 6C:
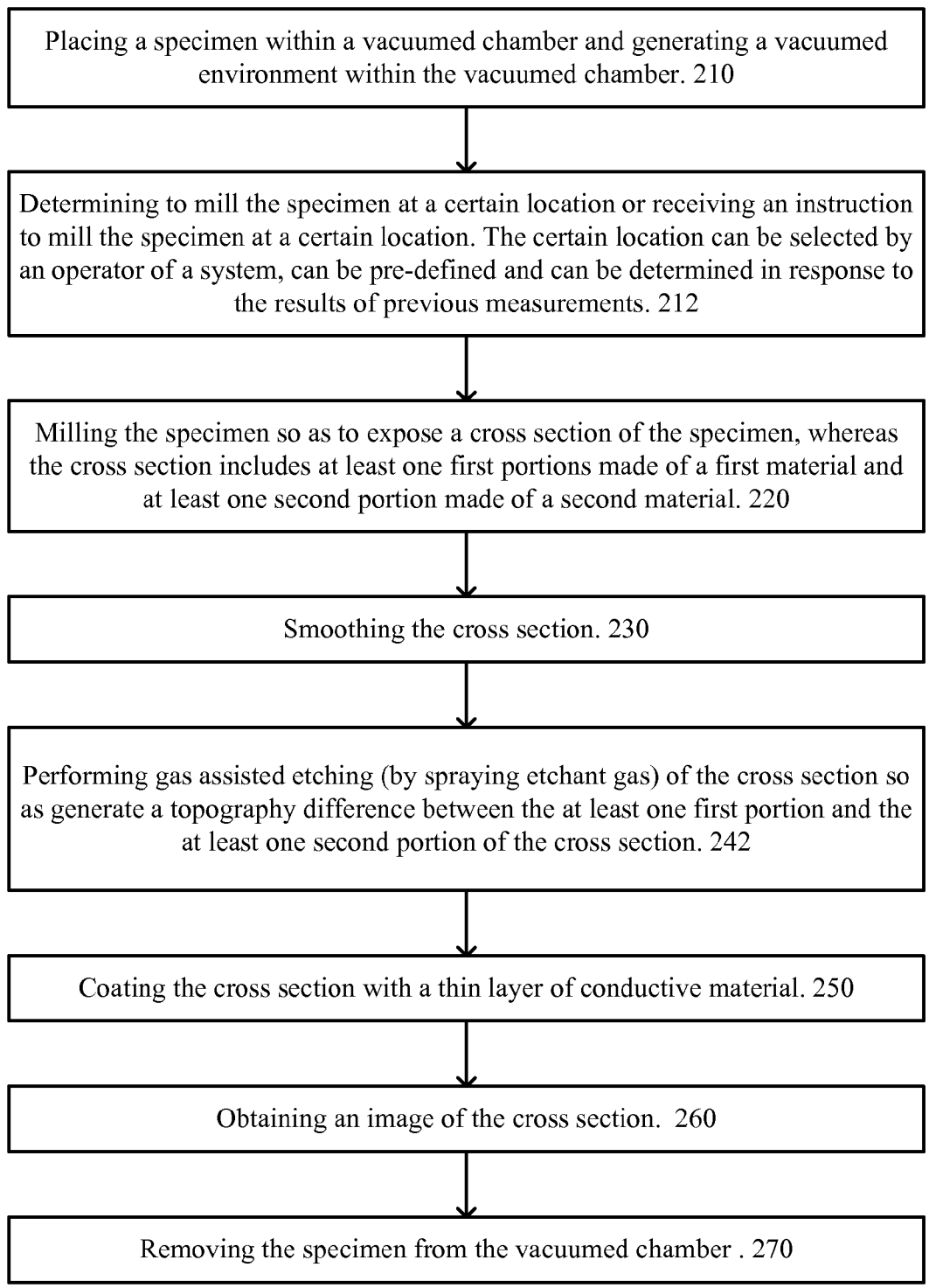
FIG. 6c illustrates a method for imaging a cross section of a specimen according to a further embodiment of the invention.

FIG. 6c illustrates method 202 for imaging a cross section of a specimen according to an embodiment of the invention.

Method 202 starts by stage 210 of placing a specimen within a vacuum chamber and generating a vacuumed environment within the vacuum chamber. Stages 220, 230, 242, 250 and 260 are executed while the specimen is located within the vacuum chamber. Conveniently, one or more cross sections are formed and imaged without removing the specimen from the vacuum chamber.

Method 202 also includes stage 212 of determining to mill the specimen at a certain location or receiving an instruction to mill the specimen at a certain location. The certain location can be selected by an operator of a system, can be pre-defined and can be determined in response to the results of previous measurements. Stage 212 can precede stage 210, can follow stage 210 and can be executed in parallel to stage 210. For simplicity of explanation, stage 212 is illustrated as following stage 210.

Stage 212 is followed by stage 220 of milling the specimen so as to expose a cross section of the specimen, in which the cross section includes at least one first portion made of a first material and at least one second portion made of a second material. Stage 220 can include locating the location to be milled and then milling that location to expose the cross section by utilizing a charge particle beam.

Stage 220 is followed by stage 230 of smoothing the cross section.

Stage 230 is followed by stage 242 of performing gas assisted etching (by spraying etchant gas) of the cross section so as generate a topography difference between the at least one first portion and the at least one second portion of the cross section.

Stage 242 is followed by stage 250 of coating the cross section with a thin layer of conductive material. Stage 250 can involve gas assisted coating.

Stage 250 is followed by stage 260 of obtaining an image of the cross section.

It is noted that stage 260 can be followed by removing the specimen from the vacuum chamber (stage 270) or can be followed by stage 220 so that another cross section is formed and imaged.

It is further noted that method 202 can be executed by system 12 but this is not necessarily so. For example, a single charged particle beam column system can implement method 202.

Conveniently, stage 220 of milling includes milling the specimen by a focused ion beam generated by a focused ion beam column that is coupled to the vacuum chamber. Conveniently, stage 260 includes illuminating the cross section by an electron beam generated by a scanning electron microscope column that is coupled to the vacuum chamber. The scanning electron microscope column can be substantially parallel to the focused ion beam column.

The present invention can be practiced by employing conventional tools, methodology and components. Accordingly, the details of such tools, component and methodology are not set forth herein in detail. In the previous descriptions, numerous specific details are set forth, in order to provide a thorough understanding of the present invention. However, it should be recognized that the present invention might be practiced without resorting to the details specifically set forth.

Only exemplary embodiments of the present invention and but a few examples of its versatility are shown and described in the present disclosure. It is to be understood that the present invention is capable of use in various other combinations and environments and is capable of changes or modifications within the scope of the inventive concept as expressed herein.

What is claimed is:

1. A method for obtaining an image of a cross section of a specimen, the method comprising:

milling the specimen using an electron beam at a first acceleration voltage generated by a scanning electron microscope (SEM) column so as to expose a cross section of the specimen, wherein the cross section comprises at least one first portion made of a first material and at least one second portion made of a second material; thereafter smoothing the cross section using an electron beam at a second acceleration voltage generated by the SEM column, the second acceleration voltage being less than the first acceleration voltage;

performing gas assisted etching of the cross section so as to generate a topography difference between the at least one first portion and the at least one second portion of the cross section;

coating the cross section with a thin layer of conductive material; and obtaining the image of the cross section using a focused ion beam generated by a focused ion beam (FIB) column, wherein the SEM column and the FIB column are coupled to a vacuum chamber, and the steps of milling, smoothing, performing, coating and obtaining are performed while the specimen is located in the vacuum chamber.

2. The method according to claim 1, wherein the SEM column and the FIB column are substantially parallel to each other and are spaced apart from each other, and the method comprises moving the specimen between a location in which the specimen is within a field of view of the SEM column to a location in which the specimen is located within a field of view of the FIB column.

3. The method according to claim 1, wherein the coating comprises performing gas assisted coating.

4. The method according to claim 1, wherein performing the gas assisted etching comprises spraying an etchant gas onto an area that is either proximate to the cross section or comprises the cross section.

5. The method according to claim 1, wherein performing the gas assisted etching comprises exposing a light activated etchant gas to light.

6. The method according to claim 5, wherein the light is focused onto an area that is either proximate to the cross section or comprises at least a portion of the cross section.

7. The method according to claim 6, wherein the area is located within a field of view of the FIB column.

8. The method according to claim 6, wherein the area is located outside a field of view of the FIB column.

9. The method according to claim 5, wherein the light activated etchant gas is exposed to light having a wavelength that does not exceed 200 nanometers.

10. The method according to claim 1, wherein performing the gas assisted etching comprises exposing a charged particle beam activated etchant gas to a charged particle beam.

11. The method according to claim 1, wherein performing the gas assisted etching comprises exposing gas to a pulsed light.

12. A method for obtaining an image of a cross section of a specimen, the method comprising:
    milling the specimen using a focused ion beam at a first acceleration voltage generated by a focused ion beam (FIB) column so as to expose a cross section of the specimen, wherein the cross section comprises at least one first portion made of a first material and at least one second portion made of a second material; thereafter
    smoothing the cross section using a focused ion beam at a second acceleration voltage generated by the FIB column, the second acceleration voltage being less than the first acceleration voltage;
    performing gas assisted etching of the cross section so as to generate a topography difference between the at least one first portion and the at least one second portion of the cross section;
    coating the cross section with a thin layer of conductive material; and
    obtaining the image of the cross section using an electron beam generated by a scanning electron microscope (SEM) column, wherein the SEM column and the FIB column are coupled to a vacuum chamber and positioned substantially parallel to each other and spaced apart from each other, and the steps of milling, smoothing, performing, coating and obtaining are performed while the specimen is located in the vacuum chamber, and wherein the method comprises moving the specimen between a location in which the specimen is within a field of view of the SEM column to a location in which the specimen is located within a field of view of the FIB column.

13. The method according to claim 12, wherein performing the gas assisted etching comprises exposing a light activated etchant gas to light.

14. The method according to claim 13, wherein the light is focused onto an area that is either proximate to the cross section or comprises at least a portion of the cross section.

15. The method according to claim 14, wherein the area is located within a field of view of the SEM column.

16. The method according to claim 14, wherein the area is located outside a field of view of the SEM column.

17. The method according to claim 13, wherein the light activated etchant gas is exposed to light having a wavelength that does not exceed 200 nanometers.

18. The method according to claim 12, wherein performing the gas assisted etching comprises exposing a charged particle beam activated etchant gas to a charged particle beam.

19. The method according to claim 12, wherein performing the gas assisted etching comprises exposing gas to a pulsed light.

20. The method according to claim 12, wherein the coating comprises performing gas assisted coating.

21. The method according to claim 12, wherein performing the gas assisted etching comprises spraying an etchant gas onto an area that is either proximate to the cross section or comprises the cross section.

* * * * *